United States Patent
Kondou et al.

(10) Patent No.: US 7,872,399 B2
(45) Date of Patent: Jan. 18, 2011

(54) ULTRASONIC PROBE AND ULTRASONIC DIAGNOSIS APPARATUS

(75) Inventors: Masanao Kondou, Tokyo (JP); Katsunori Asafusa, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 234 days.

(21) Appl. No.: 12/093,154

(22) PCT Filed: Nov. 10, 2006

(86) PCT No.: PCT/JP2006/322467
§ 371 (c)(1),
(2), (4) Date: May 9, 2008

(87) PCT Pub. No.: WO2007/055320
PCT Pub. Date: May 18, 2007

(65) Prior Publication Data
US 2009/0251025 A1    Oct. 8, 2009

(30) Foreign Application Priority Data
Nov. 11, 2005    (JP) .............................. 2005-327364

(51) Int. Cl.
*A61B 8/00*    (2006.01)
(52) U.S. Cl. ........................ 310/334; 600/459; 600/347; 367/138
(58) Field of Classification Search ................. 310/334; 73/596, 597, 599, 602, 627, 628, 632, 633; 600/437, 457, 459
See application file for complete search history.

(56) References Cited

U.S. PATENT DOCUMENTS

| 5,758,649 | A | 6/1998 | Iwashita et al. | |
|---|---|---|---|---|
| 6,381,197 | B1 * | 4/2002 | Savord et al. | 367/178 |
| 6,795,374 | B2 * | 9/2004 | Barnes et al. | 367/138 |
| 2007/0016020 | A1 * | 1/2007 | Oshiki et al. | 600/437 |
| 2008/0015441 | A1 * | 1/2008 | Kanda et al. | 600/459 |
| 2008/0064959 | A1 * | 3/2008 | Kanda et al. | 600/459 |
| 2009/0076392 | A1 * | 3/2009 | Oshiki et al. | 600/459 |
| 2010/0179430 | A1 * | 7/2010 | Sano et al. | 600/459 |

FOREIGN PATENT DOCUMENTS

| JP | 9-122125 | 5/1997 |
|---|---|---|
| JP | 2002-303612 | 10/2002 |
| JP | 2004-274756 | 9/2004 |
| WO | WO 2005/032374 | 4/2005 |
| WO | WO 2005-032374 A1 | 4/2005 |

* cited by examiner

*Primary Examiner*—J. SanMartin
(74) *Attorney, Agent, or Firm*—Antonelli, Terry, Stout & Kraus, LLP.

(57) ABSTRACT

A variance in transmitting/receiving sensitivity between multiple vibrational elements or transducers included in an ultrasonic probe is corrected. An ultrasonic probe in accordance with the present invention has multiple transducers, each of which includes multiple vibrational elements that each transmit or receive ultrasonic waves by converting ultrasonic waves and an electric signal into each other with a bias voltage applied thereto, set in array. The ultrasonic prove includes a transmitting/receiving sensitivity correction means that independently adjusts the bias voltage to be applied to at least two vibrational elements among the multiple vibrational elements so as to correct a variance in transmitting/receiving sensitivity between the at least two vibrational elements.

20 Claims, 17 Drawing Sheets

ULTRASONIC PROBE AND ULTRASONIC DIAGNOSIS APPARATUS

TECHNICAL FIELD

The present invention relates to an ultrasonic probe having multiple transducers, each of which transmits or receives ultrasonic waves to or from a subject, set in array.

BACKGROUND ART

Ultrasonic probes have multiple transducers, each of which converts an electric signal fed from an ultrasonic diagnosis apparatus into ultrasonic waves and transmits the ultrasonic waves to a subject, or receives reflected echoes generated from the subject and converts the echoes into a received signal, set in array. As the transducer, what employs a vibrational element whose ultrasound transmitting/receiving sensitivity varies depending on an applied bias voltage is known.

Herein, by controlling the bias voltage to be applied to electrodes of the vibrational element, the ultrasound transmitting/receiving sensitivity can be controlled (refer to, for example, patent document 1).

Patent document 1: JP-A-2004-274756

DISCLOSURE OF THE INVENTION

Problems that the Invention is to Solve

However, in the above conventional technology, even when the same bias voltage is applied, a variance in transmitting/receiving sensitivity occurs between multiple vibrational elements or transducers due to a variance derived from manufacture of the vibrational elements or a residual stress or the like. Consequently, image unevenness, deterioration of image quality, or an artifact phenomenon takes place in an ultrasonic image.

The patent document 1 implies that a variance in transmitting/receiving sensitivity of each vibrational element derived from a residual stress or the like can be corrected by adjusting a bias voltage to be applied to an ultrasonic transducer (capacitive micromachined ultrasonic transducer (cMUT)) that is produced through micromachining for constructing a vibrational element or a transducer. However, a concrete means or adjustment method for adjusting the bias voltage is not described therein. In the patent document 1, a proposal is made of a high-voltage switching circuit in which: multiple compact electronic switches are connected in series with an ultrasonic driver; ultrasonic transducers are connected between the electronic switches; and the electronic switch groups are controlled in order to selectively drive the ultrasonic transducers. However, the switching circuit is a circuit for selecting an ultrasonic transducer to be driven but does not correct a variance in transmitting/receiving sensitivity of each ultrasonic transducer.

An object of the present invention is to provide a concrete means and method for correcting a variance in transmitting/receiving sensitivity between multiple vibrational elements, vibrational element groups, or transducers which are included in an ultrasonic probe.

Means for Solving the Problems

An ultrasonic probe of the present invention for solving the foregoing problem has multiple transducers, each of which includes multiple vibrational elements that each transmit or receive ultrasonic waves by converting ultrasonic waves and an electric signal into each other with a bias voltage applied thereto, set in array, and includes a transmitting/receiving sensitivity correction means that independently adjusts a bias voltage to be applied to at least two vibrational elements among the multiple vibrational elements, and corrects a variance in transmitting/receiving sensitivity between the at least two vibrational elements.

Moreover, an ultrasonic diagnosis apparatus of the present invention for solving the foregoing problem includes: an ultrasonic probe that has multiple transducers, each of which includes at least one vibrational element that transmits or receives ultrasonic waves by converting ultrasonic waves and an electric signal into each other with a bias voltage applied thereto, set in array; a bias means that generates a DC voltage for use in feeding a bias voltage; and a transmission/reception control means that transmits or receives an electric signal to or from multiple vibrational elements. Between the bias means and the at least two vibrational elements among the multiple vibrational elements, a transmitting/receiving sensitivity correction means that independently adjusts the bias voltage to be applied to the at least two vibrational elements so as to correct a variance in transmitting/receiving sensitivity between the at least two vibrational elements is interposed.

Moreover, a transmitting/receiving sensitivity correction method of the present invention for solving the foregoing problem is implemented in an ultrasonic diagnosis apparatus including: an ultrasonic probe that has multiple transducers, each of which includes multiple vibrational elements that each transmit or receive ultrasonic waves by converting ultrasonic waves and an electric signal into each other with a bias voltage applied thereto, set in array; a bias means that generates a DC voltage for use in feeding the bias voltage; and a transmitting/receiving sensitivity correction means that corrects a variance in transmitting/receiving sensitivity between at least two vibrational elements among the multiple vibrational elements, and includes: a step of measuring the capacities of at least two vibrational elements; a step of selecting a reference vibrational element from the at least two vibrational elements; a step of obtaining a correction coefficient, which is needed to correct a variance in transmitting/receiving sensitivity between the at least two vibrational elements, on the basis of the capacity of the other vibrational element with respect to the capacity of the reference vibrational element; a step of calculating control data, which is needed to adjust the bias voltage, on the basis of the correction coefficients for the at least two vibrational elements, and storing the control data; and a step of transmitting or receiving ultrasonic waves by applying the adjusted bias voltage to each of the at least two vibrational elements on the basis of the control data.

Moreover, a preferred embodiment of a transmitting/receiving sensitivity correction method further includes: a step of detecting a received signal, which is based on transmission or reception of ultrasonic waves to or from each of at least two vibrational elements, with the same bias voltage applied to each of the at least two vibrational elements; a step of obtaining a magnitude of a change in a transmitting/receiving sensitivity of each of the at least two vibrational elements on the basis of the received signal of each of the at least two vibrational elements; a step of updating control data so as to correct the magnitude of the change of each of the at least two vibrational elements and storing the resultant control data; and a step of transmitting or receiving ultrasonic waves by applying the adjusted bias voltage to each of the at least two vibrational elements on the basis of the updated control data for each of the at least two vibrational elements.

In the above description, even when the vibrational element is replaced with a vibrational element group, a transducer, or a transducer group, the same applies thereto.

ADVANTAGE OF THE INVENTION

According to the present invention, a variance in transmitting/receiving sensitivity between multiple vibrational elements, vibrational element groups, or transducers that are included in an ultrasonic probe can be readily and highly precisely corrected. As a result, a high-quality ultrasonic image can be acquired.

BEST MODE FOR CARRYING OUT THE INVENTION

Referring to the drawings, embodiments of ultrasonic probes to which the present invention is applied will be described below.

First Embodiment

FIG. 1 shows an ultrasonic probe and an ultrasonic diagnosis apparatus to which the first embodiment of the present invention is applied.

As shown in FIG. 1, an ultrasonic probe includes a vibrational element 1 whose ultrasound transmitting/receiving sensitivity varies depending on an applied bias voltage, and an upper electrode 1-$a$ and a lower electrode 1-$b$ disposed with the vibrational element 1 between them.

Herein, the ultrasonic probe of the present embodiment has a transmitting/receiving sensitivity control circuit 7, which corrects a variance in transmitting/receiving sensitivity of the vibrational element 1, interposed between the vibrational element 1 and a bias means 2. Incidentally, the vibrational element 1 is generally called a cell. The number of vibrational elements 1 is not limited to one but may be increased if necessary.

The thus configured ultrasonic probe is connected to a transmission means 4 that is included in an ultrasonic diagnosis apparatus and feeds an electric signal, a reception means 5 that processes a received signal outputted from the ultrasonic probe, and the bias means 2 that includes a bias power supply (DC power supply) for applying a bias voltage to the ultrasonic probe. The transmission means 4 and reception means 5 transmit or receive a signal to or from the ultrasonic probe via a transmission/reception separation means 6. For example, a signal line and a signal return line are AC-coupled between the transmission/reception separation means 6 and vibrational element 1.

Herein, the vibrational element 1 in the present embodiment is an ultrasonic transducer whose electromechanical coupling coefficient varies depending on an applied bias voltage. For example, FIG. 1 shows an example in which a cMUT is adopted as the vibrational element 1.

The cMUT has a so-called capacitor structure having a drum-like vibrational film formed on a semiconductor substrate and having the semiconductor substrate and vibrational film sandwiched between the upper electrode 1-$a$ and the lower electrode 1-$b$. When a bias voltage is applied from the bias means 2 to the cMUT, an electric field is generated between the upper electrode 1-$a$ and the lower electrode 1-$b$. This brings the vibrational film to a tensed state.

In this state, when an electric signal transmitted from the transmission means 4 is applied to across the upper electrode 1-$a$ and the lower electrode 1-$b$, the vibrational film vibrates. Ultrasonic waves derived from the vibrations of the vibrational film are transmitted to a subject. When reflected echoes generated from the subject are inputted to the cMUT, the vibrational film vibrates to vary an internal space. Therefore, a change in the capacitance of the cMUT can be converted into as an electric signal.

Moreover, since the tension of the vibrational film varies depending on a bias voltage applied to the cMUT, when the intensity of ultrasonic waves transmitted from the cMUT to the subject is weighted by controlling the bias voltage, whether the ultrasonic waves are intense or feeble can be controlled. Likewise, a receiving sensitivity at which the cMUT receives ultrasonic waves reflected from the subject can be controlled by controlling the bias voltage. Qualitatively, the bias voltage and the transmitted wave intensity or receiving sensitivity have a substantially proportional relationship. In other words, as the bias voltage is raised, the transmitted wave intensity or receiving sensitivity increases. As the bias voltage is lowered, the transmitted wave intensity or receiving sensitivity decreases.

Although a description has been made by taking the cMUT for instance, the present invention is not limited to the example. The present invention can be applied to an element formed using an electrostrictive material characteristic of having the electromechanical coupling coefficient varied depending on a bias voltage.

The vibrational element 1 has the upper electrode 1-$a$ formed on the apex thereof and has the lower electrode 1-$b$ formed on the bottom thereof. The upper electrode 1-$a$ is connected to the positive electrode side of the bias means 2 through a terminal 2-$a$. The lower electrode 1-$b$ is connected to the negative electrode side of the bias means 2 through a terminal 2-$b$. The transmitting/receiving sensitivity control circuit 7 serving as a transmitting/receiving sensitivity correction means is interposed between the vibrational element 1 and the bias means 2 on a conductor over which a bias voltage is applied to the vibrational element 1 on the basis of a DC voltage fed from the bias means 2. Preferably, the transmitting/receiving sensitivity control circuit 7 is disposed on the side of the bias means 2 beyond a connected position, at which the transmission means 4 or reception means and the transmission/reception separation means 6 are connected to the vibrational element 1, on the conductor.

An equivalent circuit of the vibrational element 1 is, as shown in FIG. 1, expressed with a model having a capacitor Ccell and a resistor Rcell connected in parallel with each other. The capacitance Ccap of the capacitor Ccell is expressed by an equation (1) below on the assumption that a dielectric constant is $\in$, an electrode area is S, and an inter-electrode distance is d.

$$C\text{cap} = \in \cdot S/d \tag{1}$$

A charge Q stored in the capacitor Ccell has a relationship of Q=Ccap·Vdc established with the capacitance Ccap of the vibrational element 1 and a voltage Vdc fed from the bias means 2. An equation (2) below is drawn out using the equation (1).

$$Q = C\text{cap} \cdot Vdc = \in \cdot (S/d) \cdot Vdc \tag{2}$$

Herein, assuming that the equation (2) expresses the property of a reference vibrational element, a vibrational element whose inter-electrode distance or electrode area is slightly different from that of the reference vibrational element may be produced due to an effect of a residual stress or the like occurring at a step of sputtering or the like in the process of manufacturing the cMUT cell. Assuming that the capacitive component is C'cap, a charge Q' present in the vibrational element whose inter-electrode distance or electrode area is slightly different from that of the reference vibrational element is expressed by an equation (3) below.

$$Q'=C'cap \cdot Vdc \quad (3)$$

Specifically, since the capacitance of each vibrational element is slightly different from another, a charge stored therein is slightly different. In order to eliminate the effect of a variance in transmitting/receiving sensitivity, the charge Q' has to be controlled and approached to the charge Q serving as a reference. When a certain coefficient k is used to express the relationship between Q and Q', an equation (4) below is deduced. Herein, k denotes a correction coefficient between vibrational elements.

$$Q=k \cdot Q' \quad (4)$$

Next, the equation (2) is deformed using the equations (3) and (4), whereby an equation (5) below is obtained.

$$\begin{aligned} Q &= Ccap \cdot Vdc \quad (5) \\ &= k \cdot Q' \\ &= k \cdot (C'cap \cdot Vdc) \\ &= C'cap \cdot (k \cdot Vdc) \end{aligned}$$

According to the equation (5), it is understood that a variance in transmitting/receiving sensitivity between vibrational elements or even between the reference vibrational element and a vibrational element whose capacitance is different from that of the reference vibrational element can be suppressed by controlling a bias voltage, which is applied to the vibrational element, so that the bias voltage will be a product of kVdc. From the equation (5), k is generally expressed as follows:

$$k=Ccap/C'cap \quad (6)$$

Consequently, k is determined with the ratio between the capacitance of the reference vibrational element and the capacitance of another vibrational element.

FIG. 1 shows the first embodiment of the transmitting/receiving sensitivity control circuit 7 of the present invention. The present embodiment corrects a variance in transmitting/receiving sensitivity of a vibrational element by disposing a resistive element between the vibrational element and bias means and adjusting a bias voltage to be applied to the vibrational element.

To be more specific, as shown in FIG. 1, a resistor 9 whose resistance value is Rs is disposed in series between the vibrational element 1 and the positive electrode of the bias means 2. In this case, assuming that a bias voltage is Vdc, an inter-electrode voltage of the vibrational element 1 is V, and the resistance value of the vibrational element 1 is Rcell, V is expressed by an equation (7) below.

$$V=Rcell \cdot Vdc/(Rs+Rcell) \quad (7)$$

Specifically, due to voltage division by the series resistor Rs and the resistor Rcell of the vibrational element, the voltage V lower than Vdc is applied to the vibrational element (that is, a bias voltage to be applied to the vibrational element is controlled with a voltage drop caused by the series resistor Rs). Consequently, by adjusting the resistance value of the resistor Rs, the bias voltage V to be applied to the vibrational element 1 can be controlled. Eventually, a variance in a charge to be stored in each vibrational element is corrected, and the charge becomes equal to a charge stored in the reference vibrational element. A variance in transmitting/receiving sensitivity between multiple vibrational elements can be suppressed. As a result, a high-quality ultrasonic image can be acquired. Adjustment of the resistance value of the resistor Rs will be described later.

Incidentally, k is expressed by an equation (8) below on the basis of the equations (5) and (7).

$$k=Rcell/(Rs+Rcell) \quad (8)$$

Specifically, when a bias voltage is, like in the present embodiment, corrected by inserting the resistor Rs in series, $k \leq 1$ is established, and $Ccap \leq C'cap$ is deduced from the equation (6). In the present embodiment, a vibrational element whose capacitance Ccell is minimum is selected as the reference vibrational element. Namely, other vibrational elements are adapted to the vibrational element whose capacitance is minimum.

The vibrational element 1 in FIG. 1 has been described so far. The same applies to a vibrational element group 3 including, as shown in FIG. 2, multiple vibrational elements with electrodes used in common, or a transducer 8 formed, as shown in FIG. 3, by gathering multiple vibrational element groups 3. Namely, since the vibrational element group 3 is a set of multiple vibrational elements 1 and the transducer is a set of multiple vibrational element groups 3, the vibrational element group or transducer can be regarded as one large vibrational element as a whole. The transmitting/receiving sensitivity control circuit 7 is interposed between the electrodes of the vibrational element group 3 or the electrodes of the transducer 8 and the bias means 2. The transmitting/receiving sensitivity of the vibrational element group 3 or transducer 8 can be controlled by controlling a bias voltage to be applied to the vibrational element group or transducer.

The transducer can be adapted to a 1D- (where D stands for dimension), 1.5D-, or 2D-array probe transducer by modifying a connection pattern for the vibrational element group 3. Herein, a 1D array refers to a structure having an ultrasonic transducer arrayed on a one-dimensional line (straight line or a curve). A 1.5D refers to a structure having an ultrasonic transducer arrayed on a two-dimensional plane (flat plane or curved plane) defined with in a one-dimensional array direction (long-axis direction) and a direction (short-axis direction) orthogonal to the one-dimensional array direction, having ultrasonic scan and focus control performed in the long-axis direction (one-dimensional array direction), and having focus control performed in the short-axis direction (direction orthogonal to the long-axis direction).

Moreover, a 2D refers to a structure having an ultrasonic transducer arrayed on a two-dimensional plane (flat plane or curved plane), and having ultrasonic scan and focus control performed in an arbitrary direction. Namely, when all the vibrational element groups 3 of a transducer are connected to one another, the 1D-array transducer is formed. When the vibrational element groups 3 are independently handled, the 1.5D-array transducer is formed. By separating the vibrational element groups into finer vibrational element groups, the 2D-array probe transducer can be formed. What type of transducer is produced is determined in the process of manufacturing a transducer by modifying a connection pattern for vibrational element groups constituting the transducer. Incidentally, aluminum wires or the like are used to interconnect the vibrational element groups constituting the transducer.

FIG. 4 shows as another example of arrangement a case where the transmitting/receiving sensitivity control circuit 7 is connected to each of multiple transducers. FIG. 5 shows a case where one transmitting/receiving sensitivity control circuit 7 is connected to a transducer group 24 including multiple transducers. As mentioned above, the transmitting/receiving sensitivity of the transducer group 24 can be controlled by controlling a bias voltage to be applied to the transducer group 24.

Otherwise, the transmitting/receiving sensitivity of each vibrational element, each vibrational element group, or each transducer may be independently controlled in order to control a variance in transmitting/receiving sensitivity. FIG. 6 shows this example. FIG. 6 shows a case where a variance in transmitting/receiving sensitivity is corrected by independently controlling the transmitting/receiving sensitivity of each vibrational element. The illustration of the transmission means 4, reception means 5, and transmission/reception separation means 6 is omitted. In this arrangement, a resistor Rsx (where x denotes an index for each vibrational element) is added in association with each vibrational element in order to control the transmitting/receiving sensitivity of each vibrational element. Naturally, an arrangement in which the resistor Rsx is added in association with each vibrational element group or each transducer instead of each vibrational element in order to correct a variance in transmitting/receiving sensitivity of each vibrational element group or each transducer will do. Incidentally, adjustment of the resistance value of the resistor Rsx will be described later.

Now, a variance in transmitting/receiving sensitivity of each transducer will be described below. A transducer is formed by connecting multiple vibrational element groups, which are fabricated and arranged in a strip-shaped semiconductor wafer, to one another. Therefore, in the transducer 8 formed in the wafer, a variance in transmitting/receiving sensitivity occurs depending on a formed place in the wafer. Namely, a variance occurs within each transducer 8. After the transducer 8 is formed in the wafer, or at a step of assembling or mounting the completed transducer 8 in a probe, the capacitance characteristic of each of the vibrational element groups 3 constituting the transducer 8 with respect to a bias voltage is measured. FIG. 7A and FIG. 7B show examples of the results of the measurement. FIG. 7A is a graph indicating a change in a capacitance of each of the vibrational element groups d to g with respect to a bias voltage. FIG. 7B is a graph indicating a bias voltage maximizing the capacitance of each of the vibrational element groups. Based on the results of the measurement, a vibrational element group whose capacitance is maximized with a minimum bias voltage is selected. In this case, the vibrational element group g related to the minimum bias voltage Vg is selected.

Thereafter, a voltage value (hereinafter, a use permissible voltage value) designated to be slightly lower than the minimum bias voltage Vg is recorded in a memory included together with the transducer in the probe. The same measurement is performed on other transducers, and use permissible voltage values are recorded in memories included in respective probes. Thus, the use permissible voltage value inherent to the transducer of each probe is recognized. Moreover, by grasping the voltage values, a distribution of permissible use voltages of transducers fabricated using the same wafer can be grasped.

FIG. 7C shows an example. FIG. 7C is a graph indicating a distribution of use permissible voltage values of transducers within a wafer. The distribution characteristic of use permissible voltage values is used to control a variance in sensitivity between transducers. Specifically, a transducer relevant to the lowest permissible use voltage value is selected, and the permissible use voltage values of the other transducers are controlled to be equal to the permissible use voltage value of the selected transducer. In other words, an upper limit value of a bias voltage to be controlled for each transducer in order to correct a variance in transmitting/receiving sensitivity of each transducer is set to the permissible use voltage value for the transducer relevant to the lowest permissible use voltage value. In the example shown in FIG. 7C, since the permissible use voltage value relevant to the transducer G is minimum, the transducer G is selected and the permissible use voltage value is regarded as the upper limit of the bias voltage. Consequently, a variance in transmitting/receiving sensitivity between transducers within the same wafer can be suppressed with safe. The control can be attained by attaching the aforesaid transmitting/receiving sensitivity control circuit to a transducer for which a use permissible voltage should be adjusted, and controlling a bias voltage to be applied to the transducer. Adjustment of a resistance value in the control circuit will be described later.

In the above description, correction of the transmitting/receiving sensitivity of each transducer has been introduced. The transmitting/receiving sensitivity of each transducer may be corrected so that it will be equal to the transmitting/receiving sensitivity of a standard probe. What is referred to as the standard probe will be described below. In the same wafer, multiple transducer groups each of which can be mounted in a probe (hereinafter, probe transducer groups) are formed. A variance in transmitting/receiving sensitivity of each probe transducer group is measured, and a mean value of variances is then worked out. A probe transducer whose variance in transmitting/receiving sensitivity is closest to the mean value of variances is regarded as the standard probe.

Hereinafter, a vibrational element, a vibrational element group, a transducer, and a transducer group will be represented by the transducer. Noted is that even if the transducer is replaced with the vibrational element, vibrational element group, or transducer group, the same thing would be said.

Second Embodiment

FIG. 8 shows the second embodiment of the transmitting/receiving sensitivity control circuit 7 of the present invention. As illustrated, the present embodiment adopts as the transmitting/receiving sensitivity control circuit 7 a constant voltage circuit realized with an emitter follower including a transistor 10 and variable resistors $R_1$(11) and $R_2$(12), and has the transmitting/receiving sensitivity control circuit 7 interposed between the bias means 2 and transducer 8. In this circuit, a bias voltage V to be applied to the transducer 8 can be controlled by adjusting the ratio between the resistance values of the variable resistors $R_1$(11) and $R_2$(12), and a variance in transmitting/receiving sensitivity between multiple transducers can be suppressed. Adjustment of the resistance values of the variable resistors $R_1$(11) and $R_2$(12) will be described later.

Even in the present embodiment, since the bias voltage V to be applied to the transducer 8 drops to be lower than the bias voltage of the bias means 2, a transducer whose capacitance is minimum is selected as a reference transducer. The selection of the transducer, of which capacitance is minimum, as the reference transducer will be equally applied to the other embodiments to be described later.

Third Embodiment

FIG. 9 shows the third embodiment of the transmitting/receiving sensitivity control circuit 7 of the present invention. As illustrated, the present embodiment adopts as the transmitting/receiving sensitivity control circuit 7 a constant voltage circuit including an operational amplifier 13 and variable resistors $R_3(14)$ and $R_4(15)$, and has the transmitting/receiving sensitivity control circuit 7 interposed between the bias means 2 and transducer 8. Even in the present embodiment, similarly to the first and second embodiments, the bias voltage V to be applied to the transducer 8 can be controlled by adjusting the resistance values of the variable resistors $R_3(14)$ and $R_4(15)$, and a variance in transmitting/receiving sensitivity between multiple transducers can be suppressed. The adjustment of the resistance values of the variable resistors $R_3(14)$ and $R_4(15)$ will be described later.

Fourth Embodiment

FIG. 10 shows the fourth embodiment of the transmitting/receiving sensitivity control circuit 7 of the present invention. As illustrated, the present embodiment adopts as the transmitting/receiving sensitivity control circuit 7 a voltage limit circuit including a variable resistor $R_5(16)$ and a Zener diode 17, and has the transmitting/receiving sensitivity control circuit 7 interposed between the bias means 2 and transducer 8. The voltage limit circuit uses a Zener voltage characteristic of the Zener diode to control the bias voltage to be applied to the transducer 8. In other words, the resistance value of the variable resistor $R_5(16)$ is adjusted in order to adjust a current value, which flows into the Zener diode 17, so as to control the Zener voltage Vz. A variance in transmitting/receiving sensitivity between multiple transducers can therefore be suppressed. The adjustment of the resistance value of the variable resistor $R_5(16)$ will be described later.

As a variant of the embodiment 4, as shown in FIG. 11, the transmitting/receiving sensitivity control circuit 7 may be formed with a resistor 18, a Zener diode 17, and a constant current source 19. In this case, a current that flows into the Zener diode 17 corresponds to the sum of a current which flows from a bias power supply for the bias means 2 and a current which flows from the constant current source 19 for which a quantity of a current can be adjusted. Consequently, the Zener voltage Vz can be controlled by adjusting the quantity of a current flowing from the constant current source 19. The adjustment of the current value of the constant current source 19 will be described later.

Fifth Embodiment

FIG. 12 shows the fifth embodiment of the transmitting/receiving sensitivity control circuit 7 of the present invention. As illustrated, the present embodiment has the transmitting/receiving sensitivity control circuit 7 formed with a resistor 18, a constant current source 19, and a variable resistor $R_6(20)$, and has the transmitting/receiving sensitivity control circuit 7 interposed between the bias means 2 and transducer 8. In this circuit, similarly to the circuit of the variant of the embodiment 4, by adjusting a quantity of a current flowing from the constant current source 19, a current that flows into the variable resistor $R_6(20)$ is adjusted or the resistance value of the variable resistor 20 is adjusted. Consequently, the bias voltage V to be applied to the transducer 8 can be controlled, and a variance in transmitting/receiving sensitivity between multiple transducers can be suppressed. The adjustment of the resistance value of the variable resistor $R_6(20)$ will be described later.

Next, a adjustment means and method for the resistance value of a variable resistor employed in the first to fifth embodiments will be described below. The same applies to adjustment of the current value of the constant current source 19 in the fourth embodiment. The adjustment means includes a variable resistor serving as a variation means that adjusts a bias voltage and a memory in which the transmitting/receiving sensitivity characteristics of vibrational elements are stored, adjusts the variation means according to information read from the memory, and determines a value with which a variance in transmitting/receiving sensitivity can be corrected. The variation means of the adjustment means is not limited to the variable resistor. Any other means can be adopted in the same manner as long as the means can adjust the bias voltage.

A predetermined bias voltage is applied to a transducer at the time of manufacture, an impedance meter 21 is used to measure a reactance offered at a predetermined frequency. The reactance component is equivalent to the parallel capacitance between the inter-electrode capacitance of a vibrational element or a transducer and a parasitic capacitance. At this time, the capacitance is expressed by an equation (9) below.

$$C = |1/\omega X| \qquad (9)$$

where $\omega$ denotes an angular frequency.

According to the equation (9), the capacitance of a transducer is obtained based on the result of measurement of the reactance component of the transducer. The obtained capacitance and the capacitance of a transducer serving as a reference are compared with each other according to the equation (6), whereby a correction coefficient k is determined. Based on the correction coefficient k, a bias voltage to be applied to the transducer and a resistance value for obtaining the bias voltage are determined. As shown in FIG. 13, a resistor pattern produced in advance in the same wafer as the transducer is produced is subjected to trimming processing using a laser generator 22 or the like described in the publication JP-A-2004-273679 or the like. Thus, a desired resistance value is obtained.

Moreover, a variable resistive element, for example, a temperature-coefficient thermistor may be formed in a wafer. The resistance value of the thermistor itself may be adjusted by controlling the temperature of the thermistor or a current that flows into the thermistor. This utilizes the characteristic of the thermistor that the resistance value thereof varies depending on a change in temperature, and can be realized by forming a positive (or negative) temperature-coefficient thermistor and a heater in a semiconductor wafer. As an example of the heater, one employing a Peltier element and a constant current circuit is cited. The Peltier element is an element whose heating or cooling can be controlled based in the direction of a current and can have the degree thereof controlled with a quantity of a current. The combination of the constant current circuit and Peltier element provides a heater of a desired temperature and can adjust the resistance value of the thermistor. Incidentally, the present embodiment has cited the thermistor as an example of a variable resistor. Alternatively, the value of a switch-on resistor may be adjusted by controlling a gate-source voltage Vgs of a FET or the like using a DAC or the like, or a resistance value may be adjusted by controlling a current that flows into a diode.

Next, FIG. 14 shows the first control example of the transmitting/receiving sensitivity control circuit 7 of the present invention. The transmitting/receiving sensitivity control circuit 7 includes a control means 25, a memory 23, a digital-to-analog converter (hereinafter, DAC) 26, and a variable resistor 27 realized with a thermistor or the like. The memory 23 stores control data and is connected to the control means 25 over a data bus (hereinafter, bus). Moreover, the data output of the memory 23 is inputted to the DAC 26. The DAC 26 converts digital data read from the memory 23 into an analog signal, outputs the analog signal, and is connected to the variable resistor 27 formed with a thermistor or the like.

Since the other components are identical to those shown in FIG. 3, the description of the components will be omitted.

Now, concrete actions in the first control example will be described based on the flowchart of FIG. 16. The example of actions includes a transducer manufacture process, a probe assembly process, and an operation process. Programs associated with steps described below are stored in advance. When the programs associated with respective steps are read and run, the steps are automatically or semi-automatically implemented.

To begin with, the transducer manufacture process 601 to 605 will be described below. In the transducer manufacture process, control of a variance in transmitting/receiving sensitivity of each vibrational element is corrected.

At step 601, a reactance of each vibrational element at a predetermined frequency is measured in a wafer production process, and a capacitance of each vibrational element is acquired from the result of measurement.

At step 602, a reference vibrational element for use in correcting a variance in transmitting/receiving sensitivity of each vibrational element is selected. For example, a vibrational element whose capacitance is minimum is selected as the reference vibrational element.

At step 603, a correction coefficient k for use in correcting a variance in transmitting/receiving sensitivity of each vibrational element is obtained. Namely, the correction coefficient k for each vibrational element is obtained from the ratio between the capacitance of the selected reference vibrational element and the capacitance of another vibrational element.

At step 604, for each vibrational element, a resistance value (Rs) of a resistive element for use in correcting a variance in transmitting/receiving sensitivity is obtained based on the correction coefficient k. The resistance value (Rs) may be obtained using the correction coefficient k and the resistance value (Rcell) of the vibrational element according to the equation (8).

$$Rs = \{(1-k)/k\} R\text{cell} \tag{10}$$

At step 605, for each vibrational element, the resistive element exhibiting the resistance value (Rs) obtained at step 604 is mounted in the same wafer. The mounting method is, as mentioned above, a method in which the laser generator 22 or the like described in the publication JP-A-2004-273679 is used to perform trimming processing in order to obtain a desired resistance value.

At step 606, a probe transducer group is cut and extracted from the wafer.

Next, the probe assembly process 607 to 612 will be described below. In the probe assembly process, control of a variance in transmitting/receiving sensitivity of each transducer is corrected.

At step 607, a probe transducer group cut and extracted at step 606 is incorporated into a probe.

At step 608, a reactance of each transducer at a predetermined frequency is measured, and a capacitance of each transducer is acquired from the result of the measurement.

At step 609, a reference transducer for use in correcting a variance in transmitting/receiving sensitivity of each transducer is selected. As the reference transducer, for example, a transducer whose capacitance is minimum is selected.

At step 610, a correction coefficient k for use in correcting a variance in transmitting/receiving sensitivity of each transducer is obtained. Namely, the correction coefficient k for each vibrational element is obtained from the ratio between the capacitance of the selected reference transducer and the capacitance of another transducer.

At step 611, based on the correction coefficient k for each transducer, control data of a bias voltage to be applied to each transducer is calculated, and stored in the memory over the bus. Moreover, control data for each transducer and the date of production of the control data are recorded in a log file in the memory 23. Specifically, from the correction coefficient k, control data such as a current value, a voltage value, or an amount of heat (in a case where a Peltier element is adopted as a heat source, a current value that is a control factor) for use in controlling a control factor such as a resistance value is calculated for a control device such as the variable resistor 27 (for example, a thermistor) of the transmitting/receiving sensitivity control circuit 7. The control data is then stored in the memory 23 over the bus. The control data is also used to correct a variance in transmitting/receiving sensitivity after delivery of a product.

At step 612, based on the control data, the bias voltage adjusted for each transducer is applied in order to transmit or receive ultrasonic waves. When ultrasonic waves are transmitted or received, the control means 25 reads the control data stored in the memory 23, and outputs it to the DAC 26. The DAC 26 controls a current value or the like according to the value of the inputted control data so as to control the resistance value of the variable resistor 27. Specifically, when the variable resistor 27 includes a negative-temperature coefficient thermistor and a Peltier element, a current controlled by the DAC 26 is caused to flow into the Peltier element. Thus, the resistance value can be indirectly controlled through direct temperature control of the negative-temperature coefficient thermistor.

Now, a voltage applied to across the transducer 8 is a fraction of a voltage value, which is fed from the bias means 2, produced based on the resistance value Rs of the variable resistor 27 and the resistance value R of the transducer 8. Namely, a variance in transmitting/receiving sensitivity for ultrasonic waves is corrected by adjusting an electromechanical coupling coefficient dependent on an electric-field intensity. Thus, control is extended so that transducers will exhibit the same transmitting/receiving sensitivity. When transmitting/receiving sensitivity correction is performed, a display signifying that sensitivity correction is under way may appear on the screen of the ultrasonic diagnosis apparatus.

Finally, the operation process 613 to 618 will be described below. In the operation process, a deviation in control of a variance in transmitting/receiving sensitivity of each transducer derived from a time-sequential change in transmitting/receiving sensitivity of the transducer is corrected.

At step 613, the transmitting/receiving sensitivity of each transducer is measured. After delivery of a product, since it is technically hard to directly measure the capacitance of a transducer incorporated in an ultrasonic probe, the transmitting/receiving sensitivity of the transducer is indirectly measured. As an example, with the ultrasonic probe abutted against a predetermined phantom, the control means 25 detects the voltage of a response signal for a bias voltage inputted to each transducer. Thus, the control means 25 can measure the transmitting/receiving sensitivity of each transducer.

At step 614, whether a variance in transmitting/receiving sensitivity of each transducer has to be corrected is decided. For example, whether the transmitting/receiving sensitivity of each transducer falls within a range of threshold values (for example, ±1 dB of a mean of transmitting/receiving sensitivities of transducers obtained at step 613) is determined. If the transmitting/receiving sensitivity of each transducer falls outside the range, a decision is made that variance correction is needed, and processing proceeds to step 615. If the transmitting/receiving sensitivity of each transducer falls within the range of threshold values, a decision is made that variance correction is not needed, and processing proceeds to step 618.

At step 615, a reference transducer is selected for use in correcting a deviation in correction of a variance in transmitting/receiving sensitivity of each transducer. As the reference transducer, for example, a transducer whose transmitting/receiving sensitivity is minimum is selected.

At step 616, a correction coefficient k is obtained for use in correcting a deviation in correction of a variance in transmitting/receiving sensitivity of each transducer. In other words, the correction coefficient k for each vibrational element is obtained from the ratio between the transmitting/receiving sensitivity of the selected reference transducer and the transmitting/receiving sensitivity of another transducer.

At step 617, based on the correction coefficient k for each transducer, control data for a bias voltage to be applied to each transducer is updated and stored in the memory 23 over the bus. Specifically, for a transducer whose sensitivity is degraded, control data is modified so that the bias voltage to be applied to the transducer will be increased. On the other hand, for a transducer whose sensitivity is upgraded, control data is updated so that the bias voltage to be applied to the transducer will be decreased. The control means 25 updates, as mentioned above, the control data stored in the memory 23 in advance, and can thus highly precisely correct a variance in transmitting/receiving sensitivity all the time. After the control data is updated, processing returns to step 613, and the transmitting/receiving sensitivity of each transducer is measured again.

At the time of updating control data, control data for each transducer and a date of update are recorded in a log file, and the data is recorded in the memory 23. Due to a time-sequential change in transmitting/receiving sensitivity of each transducer, control data for use in controlling a control device is updated properly. The frequency or cycle of update is calculated in the control means 25 on the basis of the log file produced at the time of update. The results of the calculation can be displayed on the screen of the apparatus by depressing a button disposed on an operating console of the ultrasonic diagnosis apparatus.

Otherwise, at the time of updating control data, relative values of the transmitting/receiving sensitivities of other transducers with respect to the transmitting/receiving sensitivity of the reference transducer may be displayed on the screen, and the control data may be updated through the screen. FIG. 17 shows an example. FIG. 17 shows an example in which a data list 701 of a time-sequential change in a variance in transmitting/receiving sensitivity of each transducer, and two control buttons 702 and 703 are displayed on the screen. The data list 701 lists an ID number of each transducer, a time-sequential change of a relative value of transmitting/receiving sensitivity thereof with respect to the reference transducer from one to another, and a magnitude of calibration (%) of control data. The time-sequential change of the relative value of the transmitting/receiving sensitivity from one to another refers to time-sequential display of an initial value at the time of manufacture or assembly and relative values of transmitting/receiving sensitivities measured thereafter. If the measurement button 702 is depressed in this state, the steps 613 to 616 are executed. The relative value of the transmitting/receiving sensitivity of each transducer is measured, and a magnitude of calibration (%) of control data for bringing the relative value to 1 is calculated and displayed. After measurement of the relative values of transmitting/receiving sensitivities of all transducers and calculation of magnitudes of calibration of control data items are completed, if the application button 703 is depressed, the calculated magnitudes of calibration are reflected on the respective control data items. Moreover, the measured relative values of transmitting/receiving sensitivities are stored together with date-of-measurement data items in the memory means, and displayed on the screen at the next time of updating control data.

At step 618, based on updated control data, a adjusted bias voltage is applied to each transducer in order to transmit or receive ultrasonic waves.

At step 619, if correction of a deviation in control of a variance in transmitting/receiving sensitivity of each transducer derived from a time-sequential change in transmitting/receiving sensitivity of the transducer is repeated at regular or irregular intervals, processing returns to step 613. The steps 613 to 618 are then repeated.

As mentioned above, updated control data is used to control the transmitting/receiving sensitivity in order to transmit or receive ultrasonic waves. Consequently, with a variance in transmitting/receiving sensitivity corrected highly precisely, a high-quality ultrasonic image can be acquired all the time. In the description of the probe manufacture process and operation process, an example in which the reference transducer is selected and a variance in transmitting/receiving sensitivity of each transducer is corrected has been cited. However, the transmitting/receiving sensitivity of a standard probe may be regarded as a reference, and a variance in transmitting/receiving sensitivity between probes may be corrected.

The concrete action flow of the first control example has been described so far.

In this example, the negative-temperature coefficient thermistor is employed. Alternatively, a positive-temperature coefficient thermistor may be employed. Moreover, in the present example, the temperature-coefficient thermistor and Peltier element are used to control a resistance value. Alternatively, a current may be caused to directly flow into a self-current control thermistor. If correction of a time-sequential change at the steps 613 to 617 is not performed, control data is needed only in a wafer production process or in the probe assembly process succeeding chip formation. Therefore, the memory 23 can have the function thereof limited to reading from a nonvolatile memory element such as a ROM. A circuit scale can be reduced.

According to the first control example, correction of a variance in transmitting/receiving sensitivity of each transducer can be performed continuously and most optimally all the time. Moreover, since a control device includes a thermistor and a Peltier element, a temperature characteristic can be readily adjusted based on a kind of dopant (an impurity to be mixed, for example, boron (dope), SiC (thin film), Ge (thin film), or Ni (metal)) employed in a semiconductor process, a quantity thereof, or a thin film.

Next, FIG. 15 shows the second control example of the transmitting/receiving sensitivity control circuit 7 of the present invention. Differences from the first control example lie in that a data latch circuit 28 is substituted for the DAC 26 and that an analog switch switching type variable resistor which switches multiple analog switches realized with MOS switches or mechanical relays so as to control a resistance value is adopted as a type of variable resistor instead of the thermistor. The variable resistor can be realized with, for example, a micro-relay based on a MEMS technology or a ladder resistor. Since the other components are identical to those of the first control example, the illustration of the transducer 8 and bias means 2 will be omitted.

Now, concrete actions in the second control example will be described. An action flow in the second control example is identical to that in the first control example except the contents of control data at step 611 and the contents of step 612. Only the different parts will be described below.

At step 611, an action that the control means 25 stores control data in the memory 23 is identical to that in the first control example. However, the control data stored in the memory 23 is control data for switching switches of an analog switch switching type variable resistor.

At step 612, when ultrasonic waves are transmitted or received, the control means 25 reads control data stored in the memory 23 and outputs it to the data latch circuit 28. The data latch circuit 28 holds multiple values of control data items inputted at the timing of a latch clock, alternates the openings and closings of the analog switches according to the multiple values of control data items, and thus controls the resistance value of the variable resistor.

Even in the second control example, similarly to the first control method, if the transmitted/received signal intensity of each transducer is measured after the assembly process, correction of a variance can be performed according to a time-sequential change in each element.

Owing to the second control example, a variance in transmitting/receiving sensitivity of each transducer can be corrected without being affected by an external factor such as ambient temperature.

Incidentally, the first and second control examples can be achieved either online or offline.

As another example of correction of a variance in transmitting/receiving sensitivity after delivery of a product, verification of the situation of a variance in transmitting/receiving sensitivity of a probe and correction processing of the variance in transmitting/receiving sensitivity may be performed remotely. For this purpose, the ultrasonic diagnosis apparatus includes a communication means capable of communicating with an external control means, which is installed outside the apparatus (for example, a host computer at a remote center), over a network. The ultrasonic diagnosis apparatus is connected to a host computer, which holds correction information on the transmitting/receiving sensitivity of each probe, over the network in order to perform verification of the situation of the transmitting/receiving sensitivity dependent on a time-sequential change in each probe, update of control data inherent to the probe, and correction processing of a variance in transmitting/receiving sensitivity.

Finally, in the description of the present invention, a variance in transmitting/receiving sensitivity of each vibrational element, each vibrational element group, or each transducer is corrected. Alternatively, the transmitting/receiving sensitivity of each vibrational element, each vibrational element group, or each transducer may be corrected so that it will be equal to the sensitivity of a standard probe.

DESCRIPTION OF REFERENCE NUMERALS AND SIGNS

Figure 1:
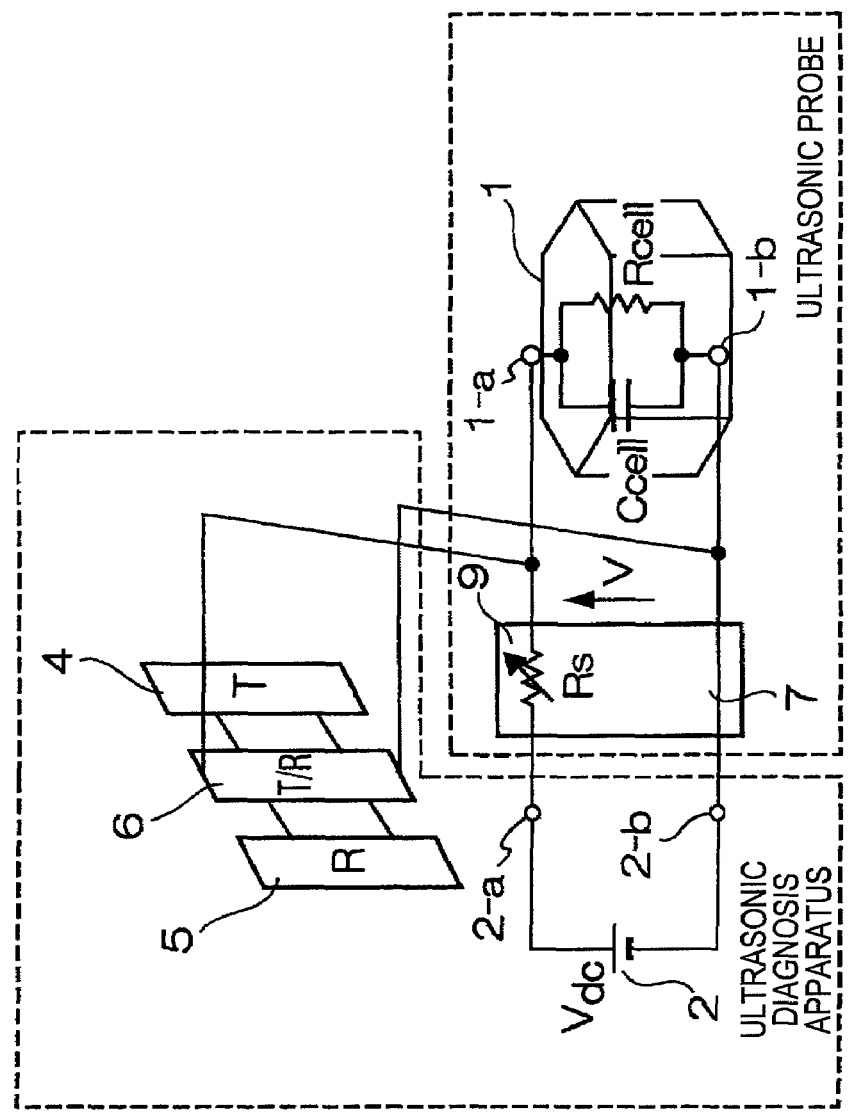
FIG. 1 shows the first embodiment of an ultrasonic probe, an ultrasonic diagnosis apparatus, and a transmitting/receiving sensitivity control circuit to which the present invention is applied.
Figure 2:
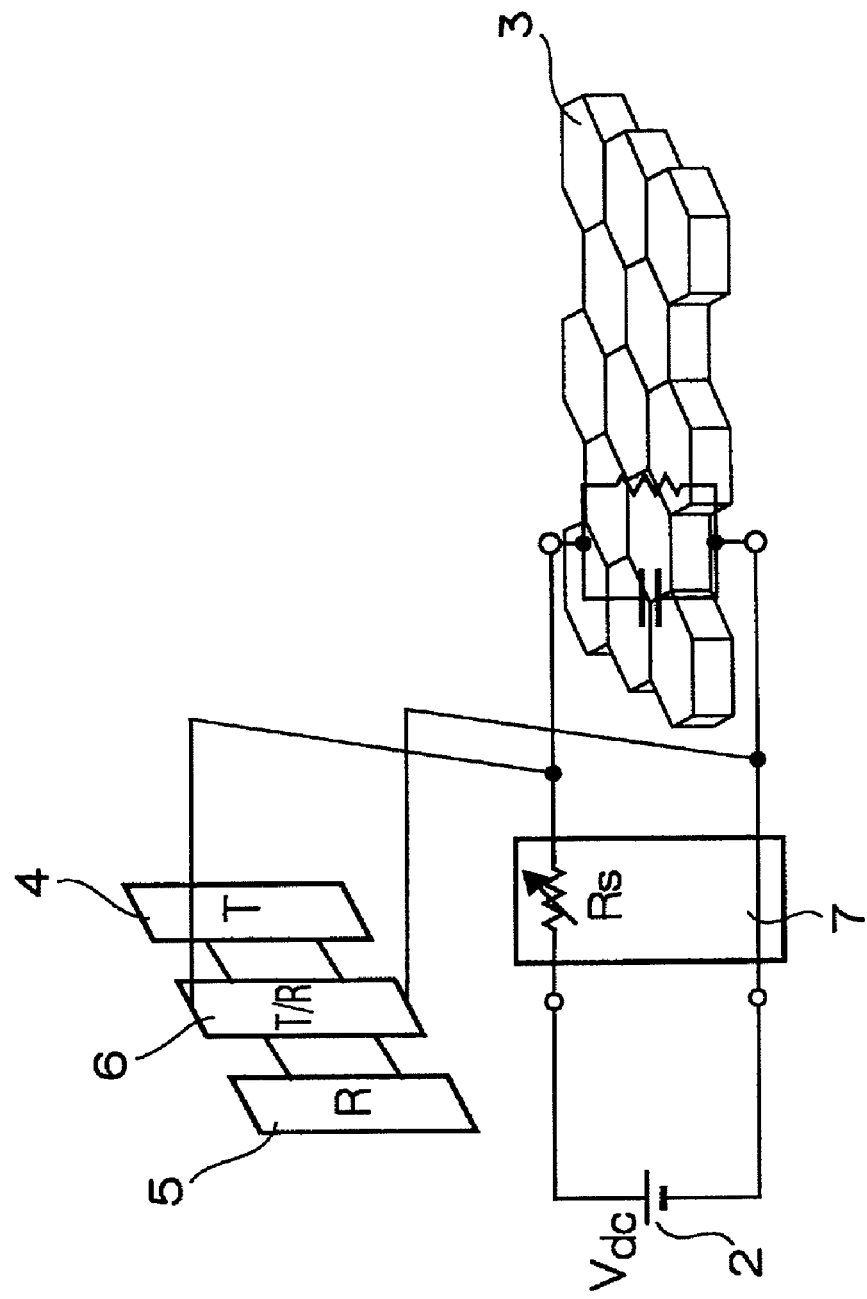
FIG. 2 shows a vibrational element shown in FIG. 1 as a vibrational element group.
Figure 3:
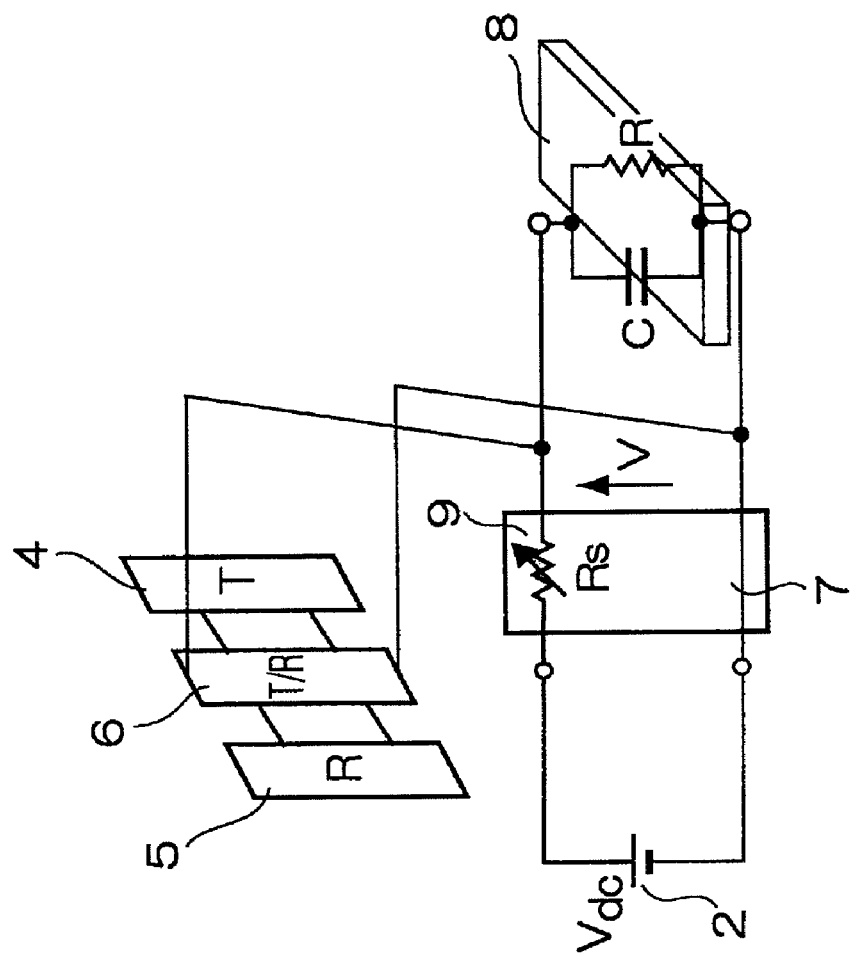
FIG. 3 shows the vibrational element shown in FIG. 1 as a transducer.
Figure 4:
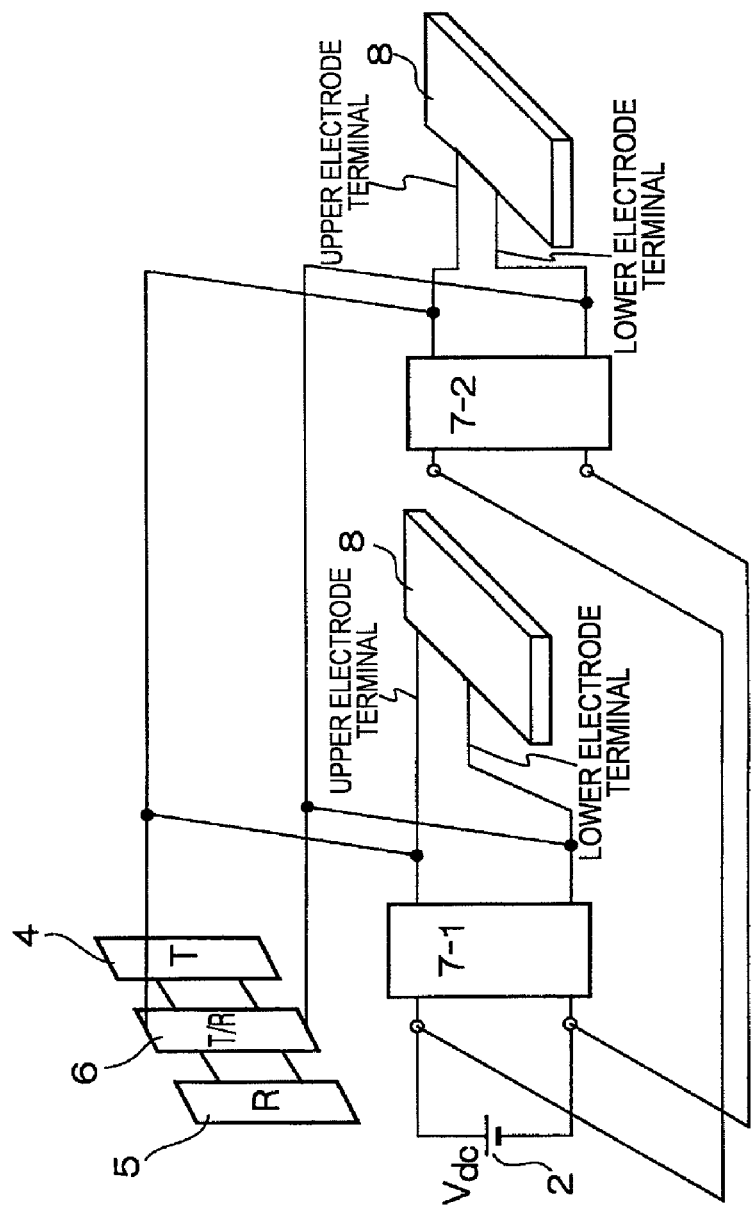
FIG. 4 shows a case where a transmitting/receiving sensitivity control circuit 7 is connected to each of multiple transducers.
Figure 5:
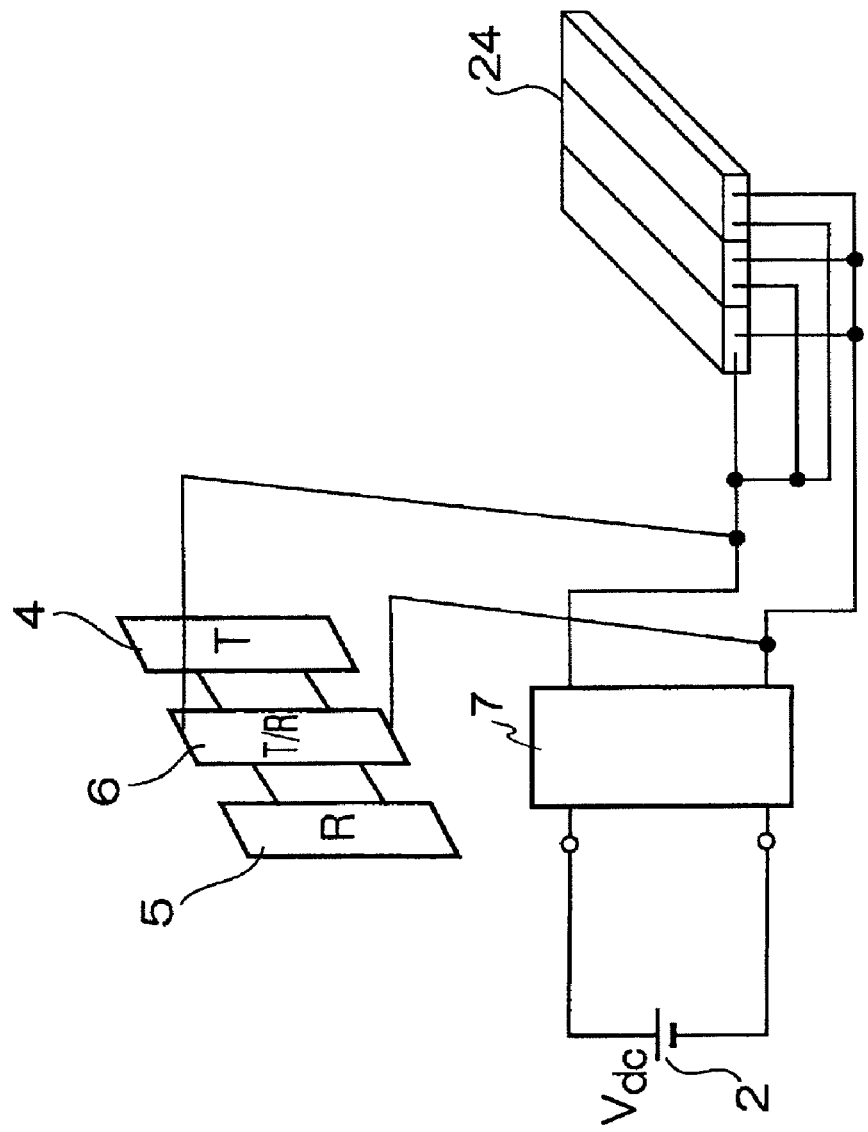
FIG. 5 shows the vibrational element shown in FIG. 1 as a transducer group.
Figure 6:
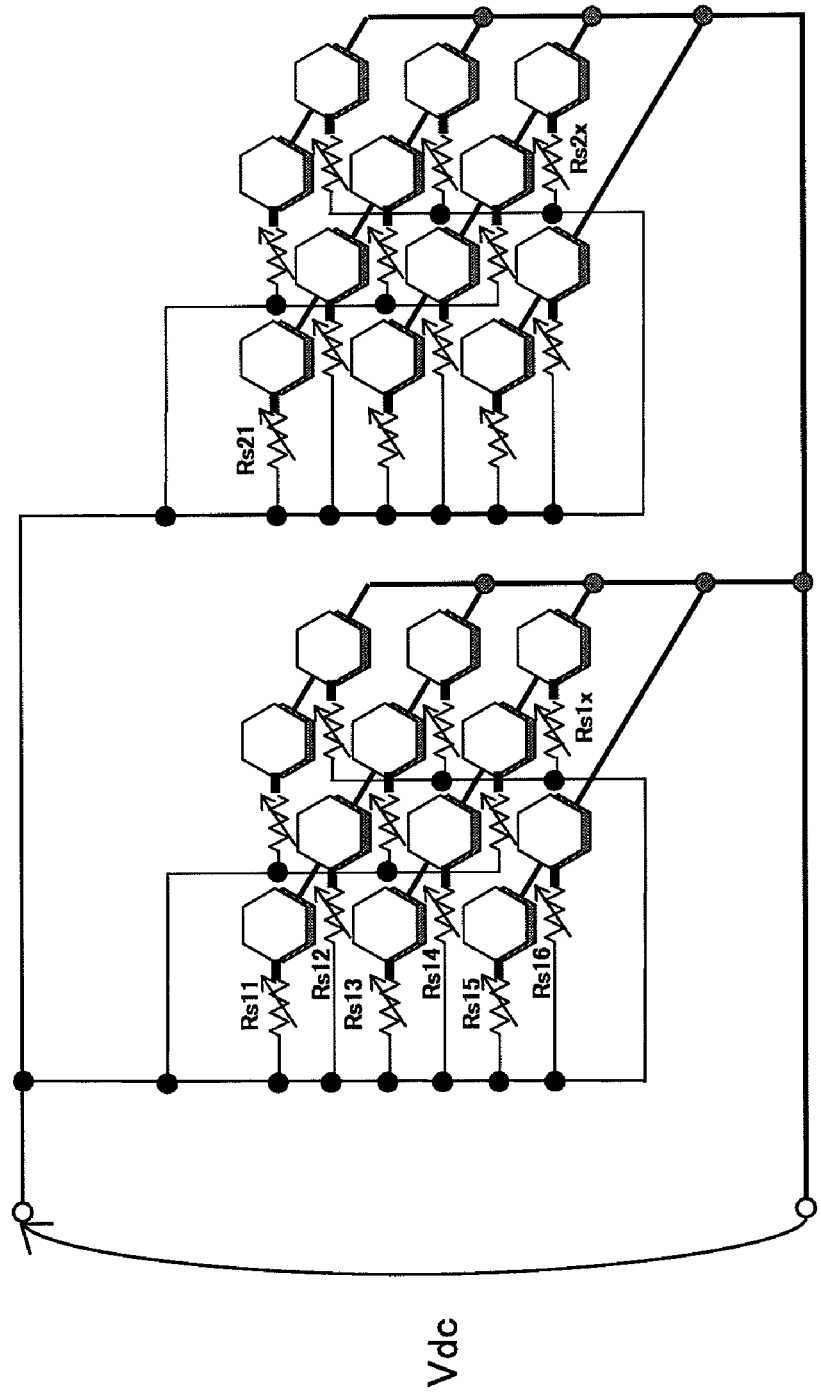
FIG. 6 shows a case where a control resistor Rx is connected to each of multiple vibrational elements.
Figure 7A:
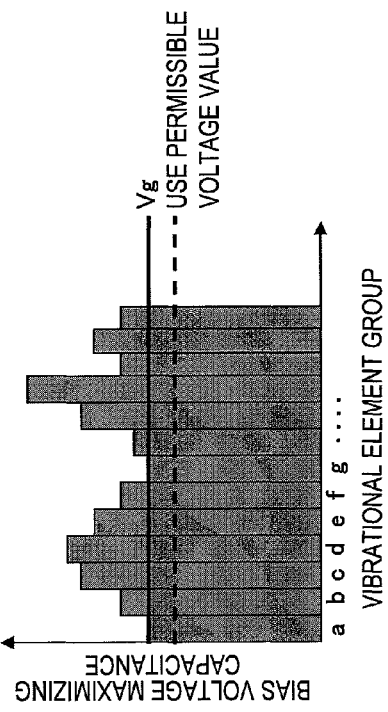
FIG. 7A shows the results of voltage-vs.-capacitance measurement performed on a vibrational element group.
Figure 7B:
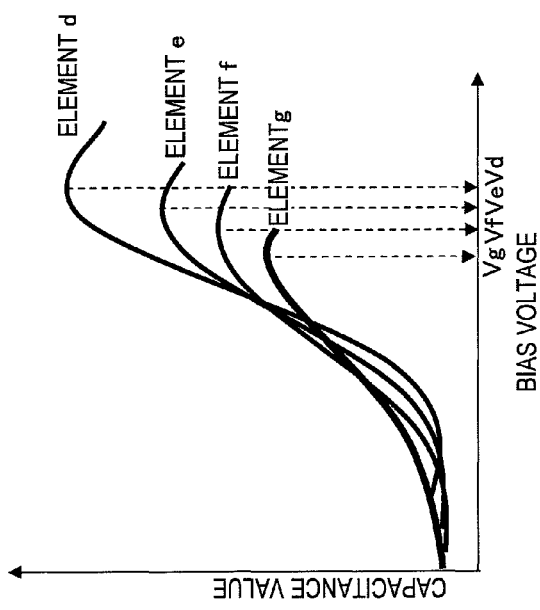
FIG. 7B shows a maximum applied voltage value for each of vibrational element groups.
Figure 7C:
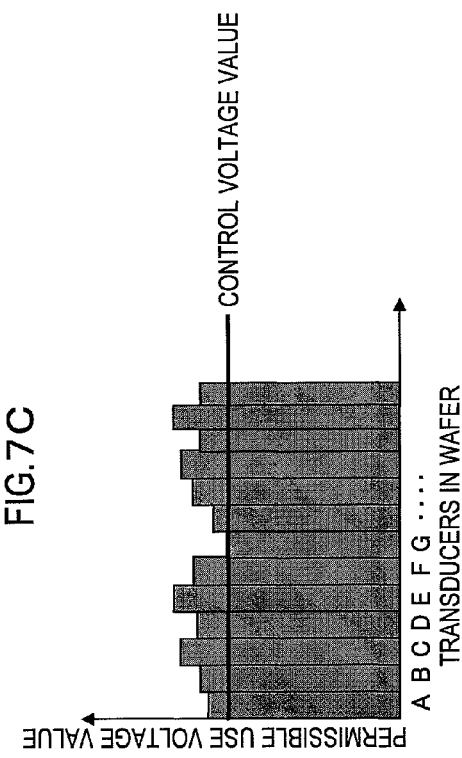
FIG. 7C shows a permissible use voltage value for each of transducers.
Figure 8:
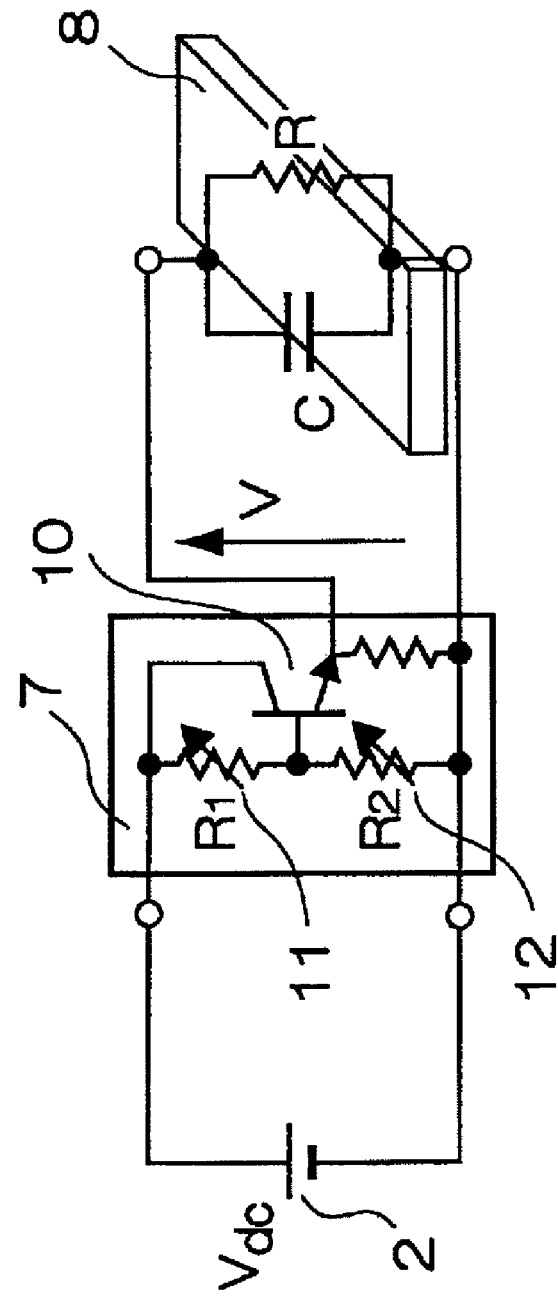
FIG. 8 shows the second embodiment of the transmitting/receiving sensitivity control circuit.
Figure 9:
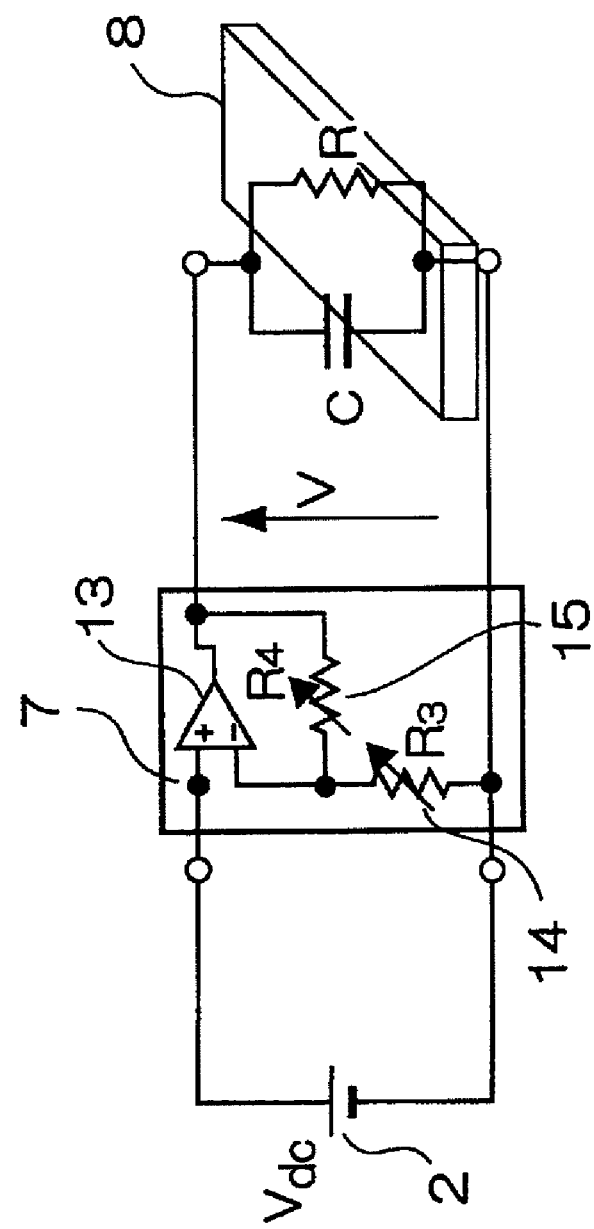
FIG. 9 shows the third embodiment of the transmitting/receiving sensitivity control circuit.
Figure 10:
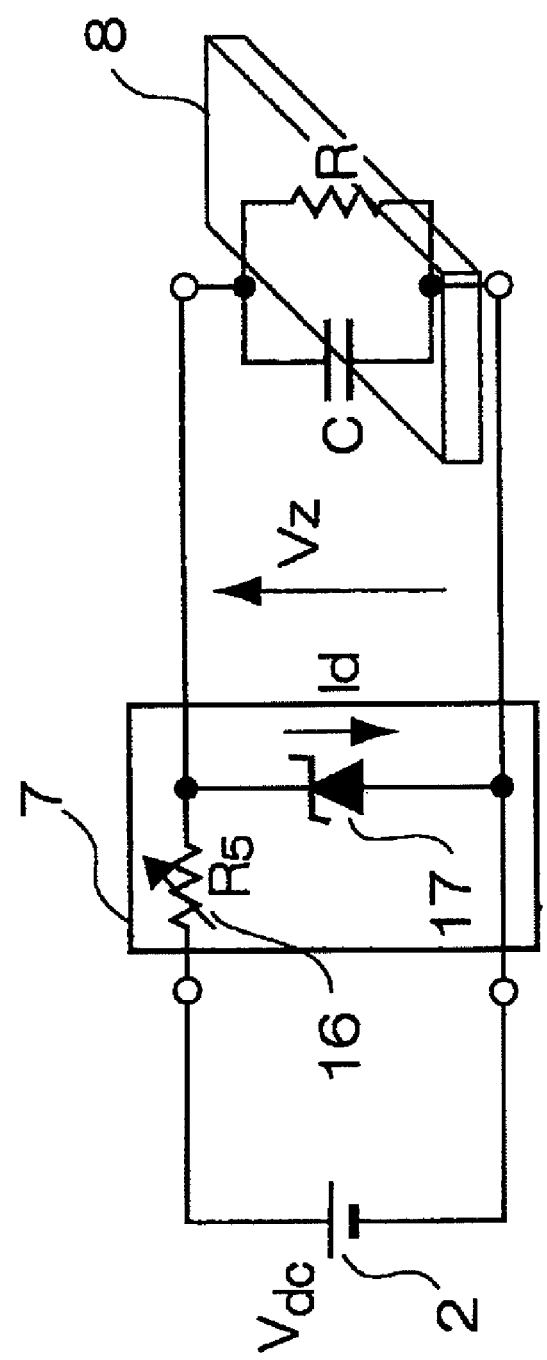
FIG. 10 shows the fourth embodiment of the transmitting/receiving sensitivity control circuit.
Figure 11:
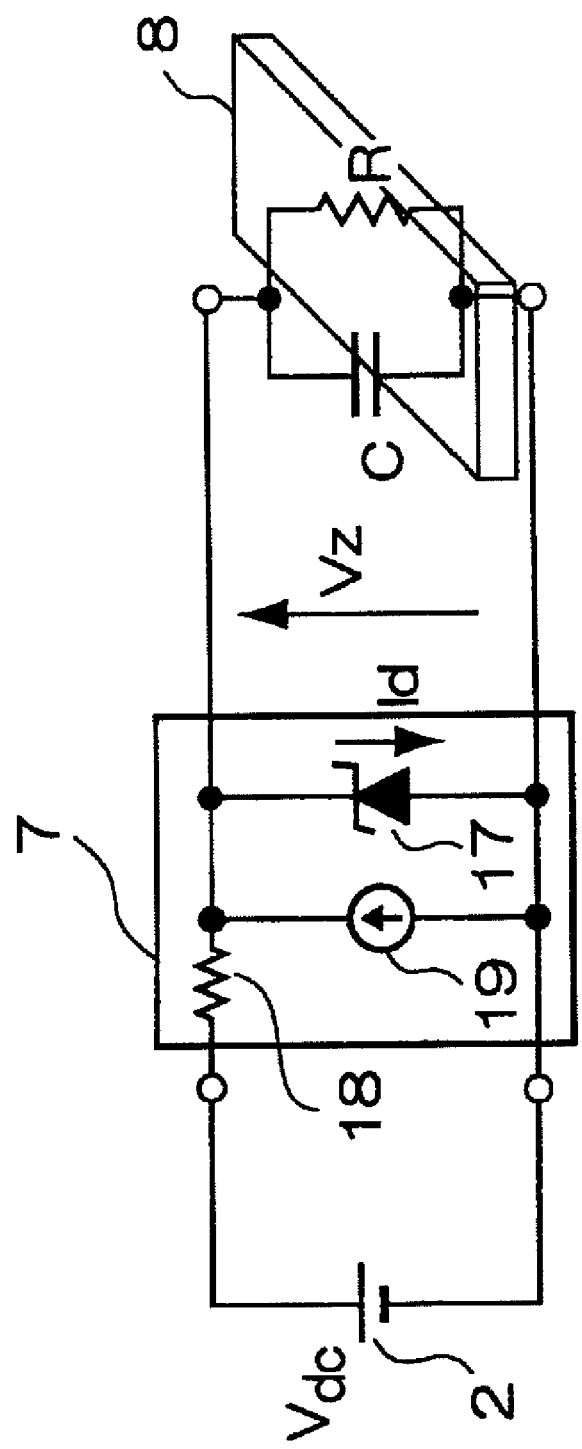
FIG. 11 shows a variant of the fourth embodiment of the transmitting/receiving sensitivity control circuit.
Figure 12:
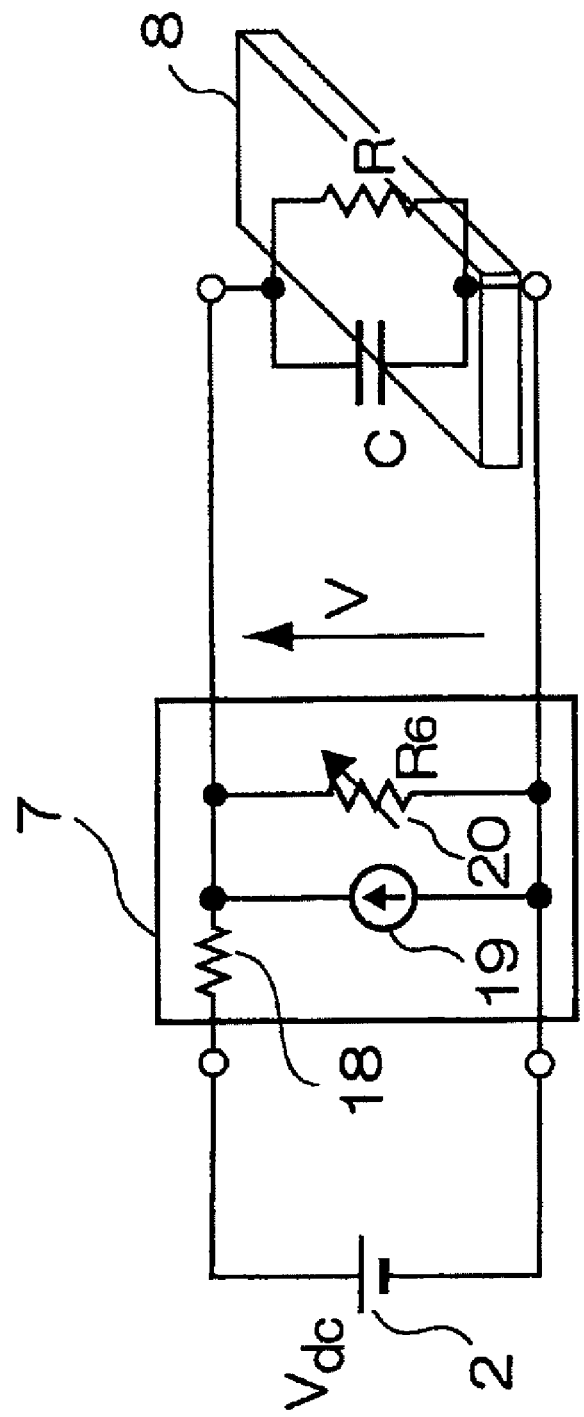
FIG. 12 shows the fifth embodiment of the transmitting/receiving sensitivity control circuit.
Figure 13:
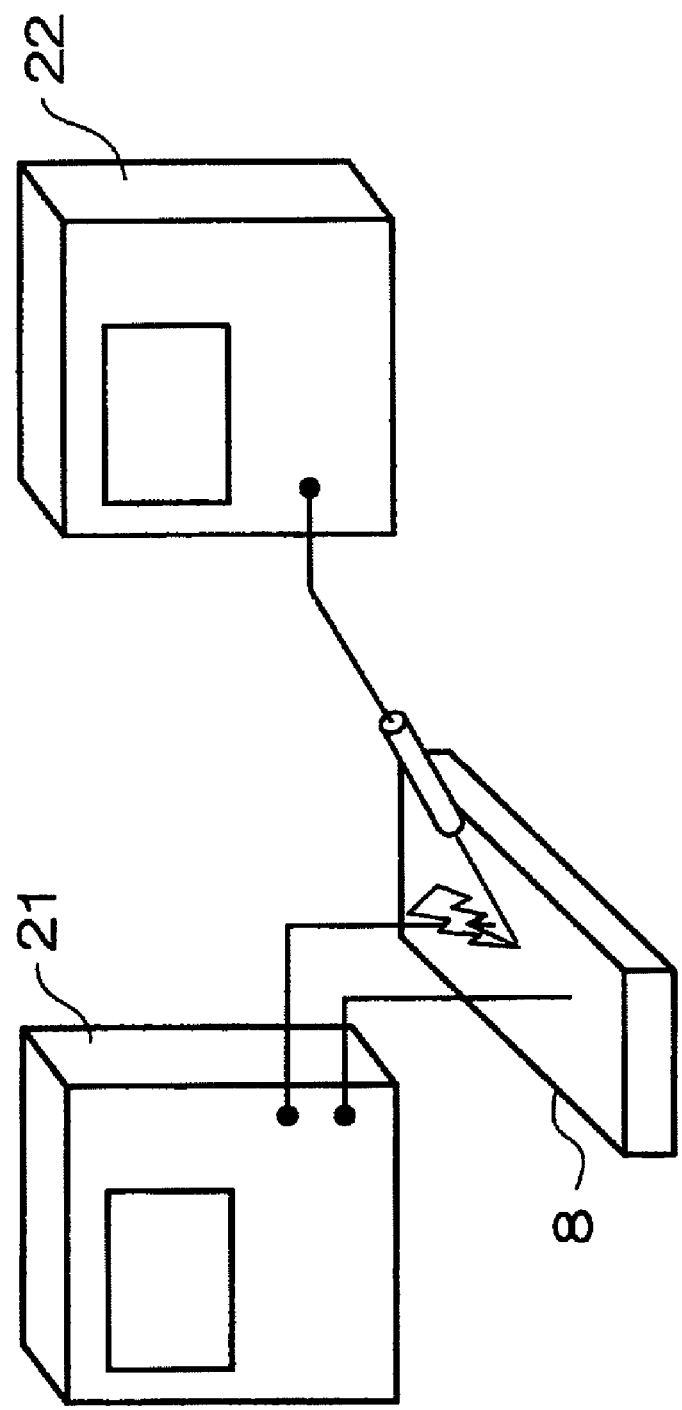
FIG. 13 shows a scene where a laser generator is used to perform trimming processing on a resistor formed on the same wafer as a vibrational element is.
Figure 14:
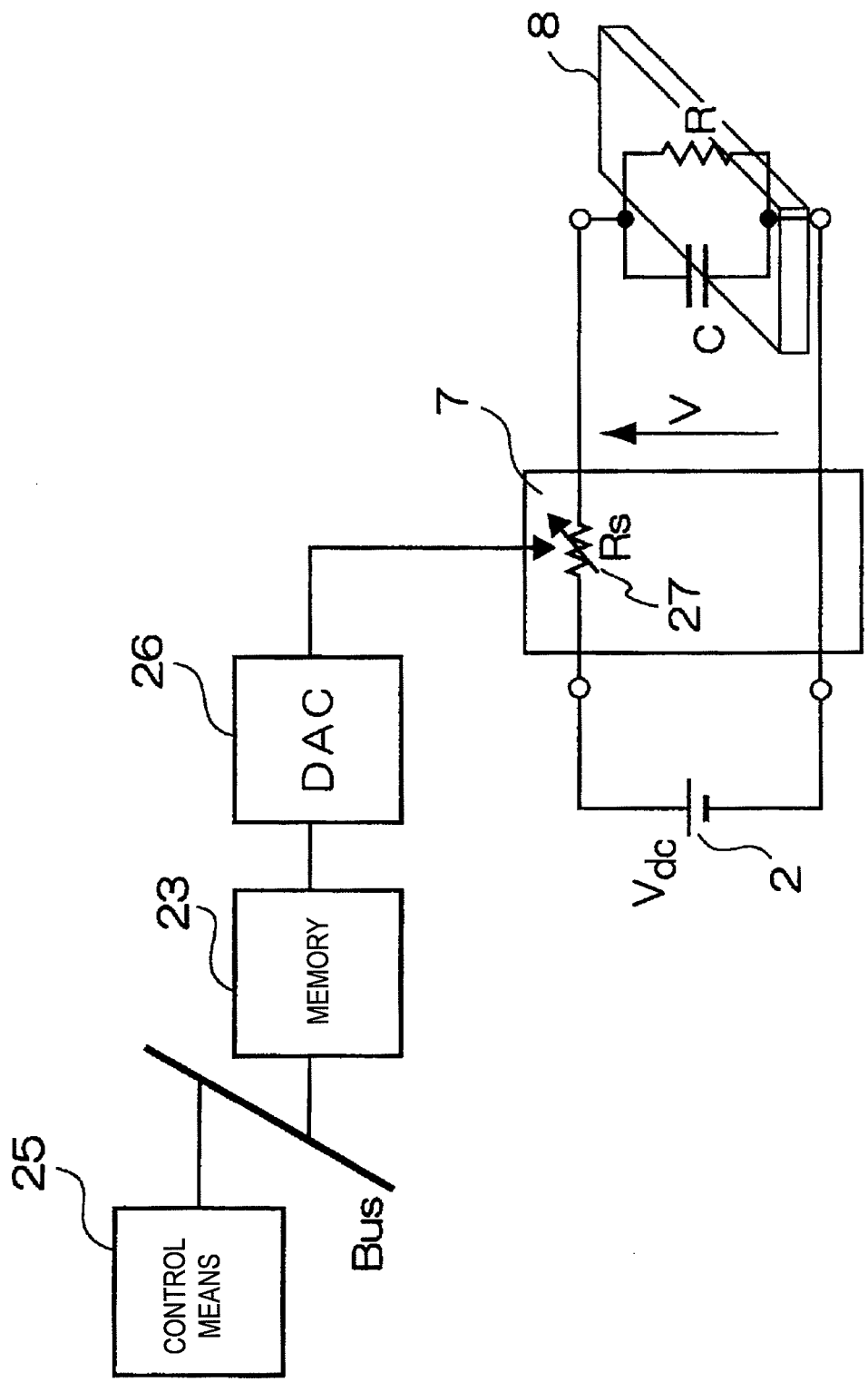
FIG. 14 shows the first control example of the transmitting/receiving sensitivity control circuit of the present invention.
Figure 15:
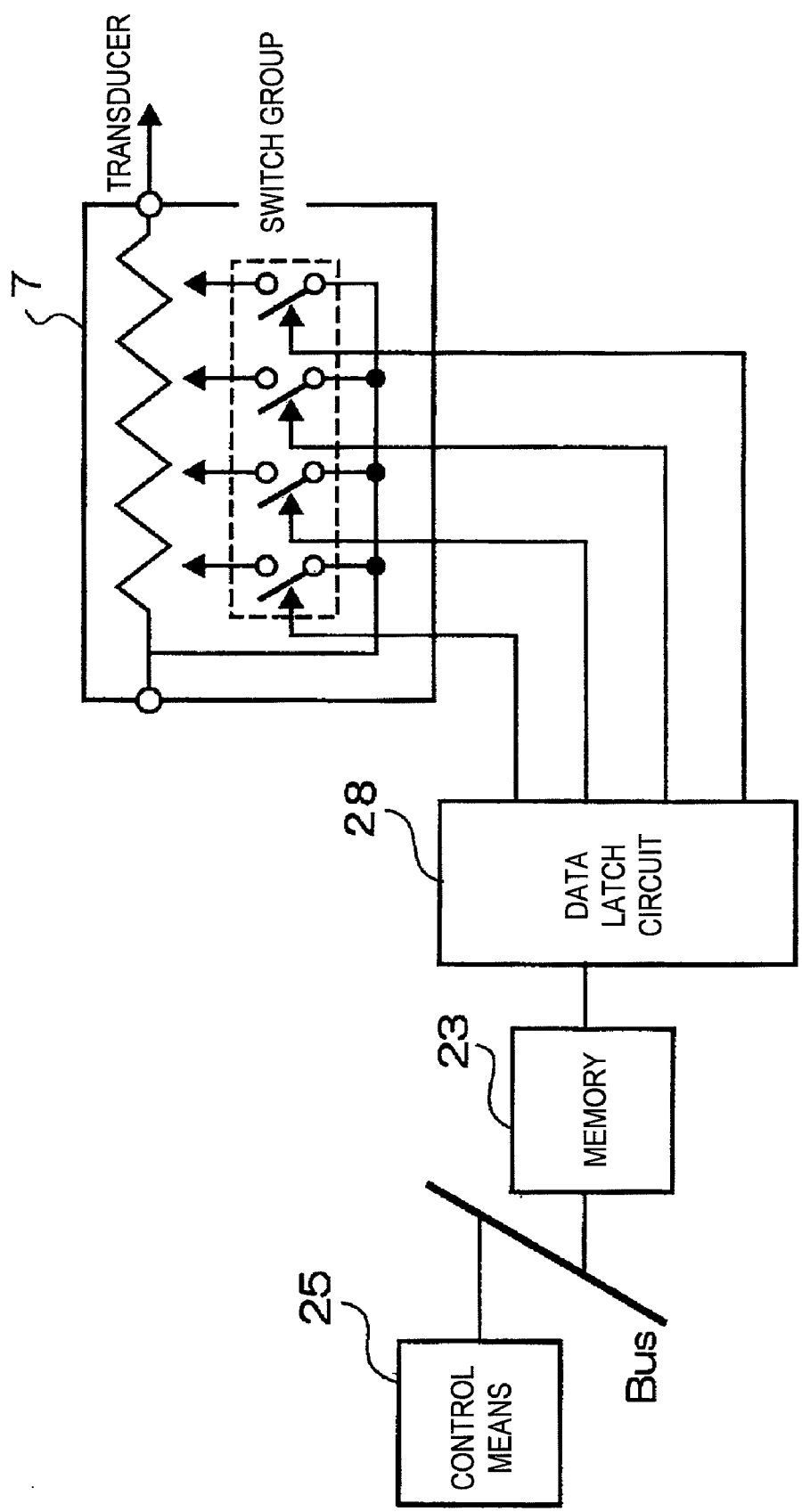
FIG. 15 shows the second control example of the transmitting/receiving sensitivity control circuit of the present invention.
Figure 16:
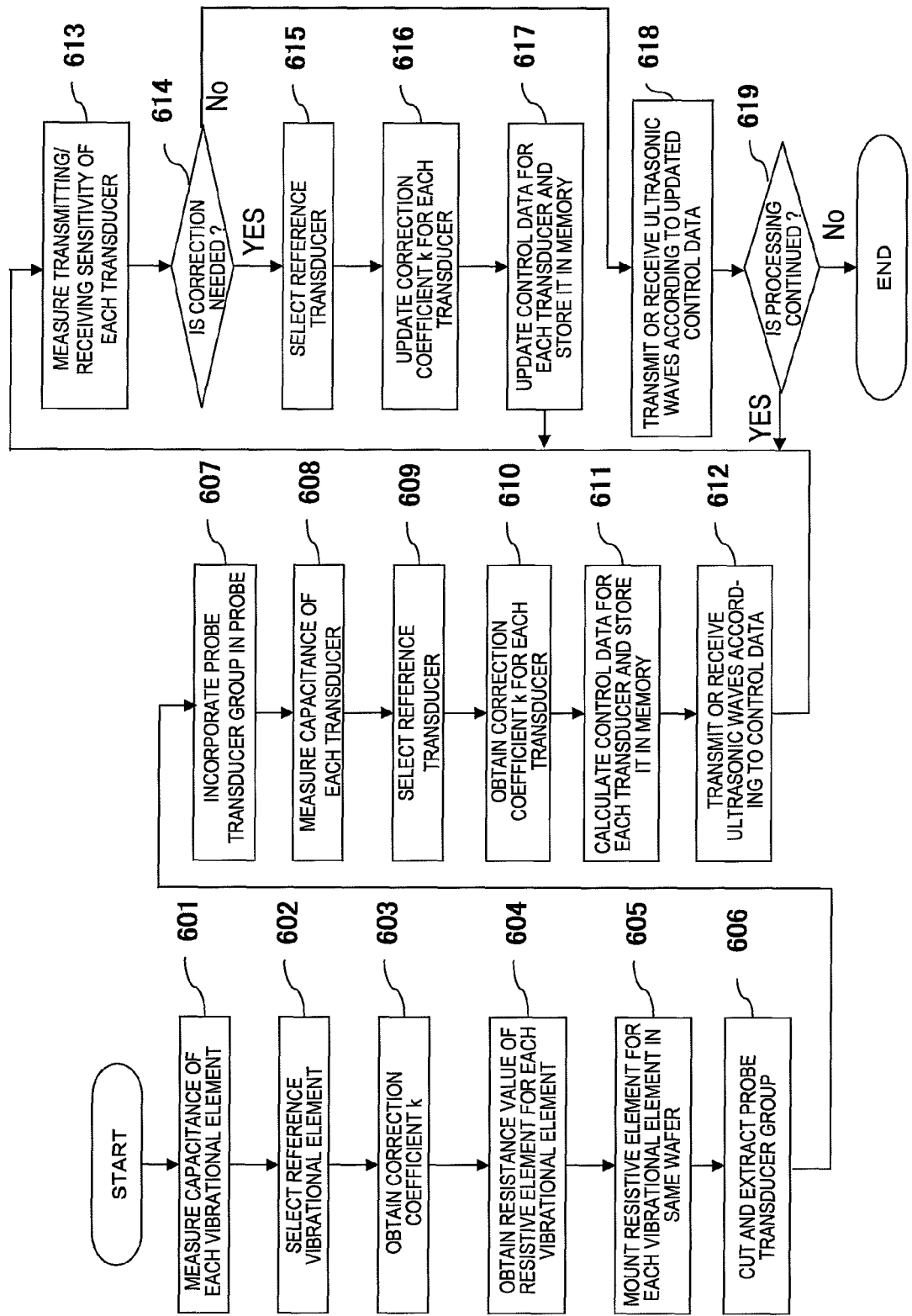
FIG. 16 is a flowchart presenting concrete actions in the first control example of the transmitting/receiving sensitivity control circuit shown in FIG. 14.
Figure 17:
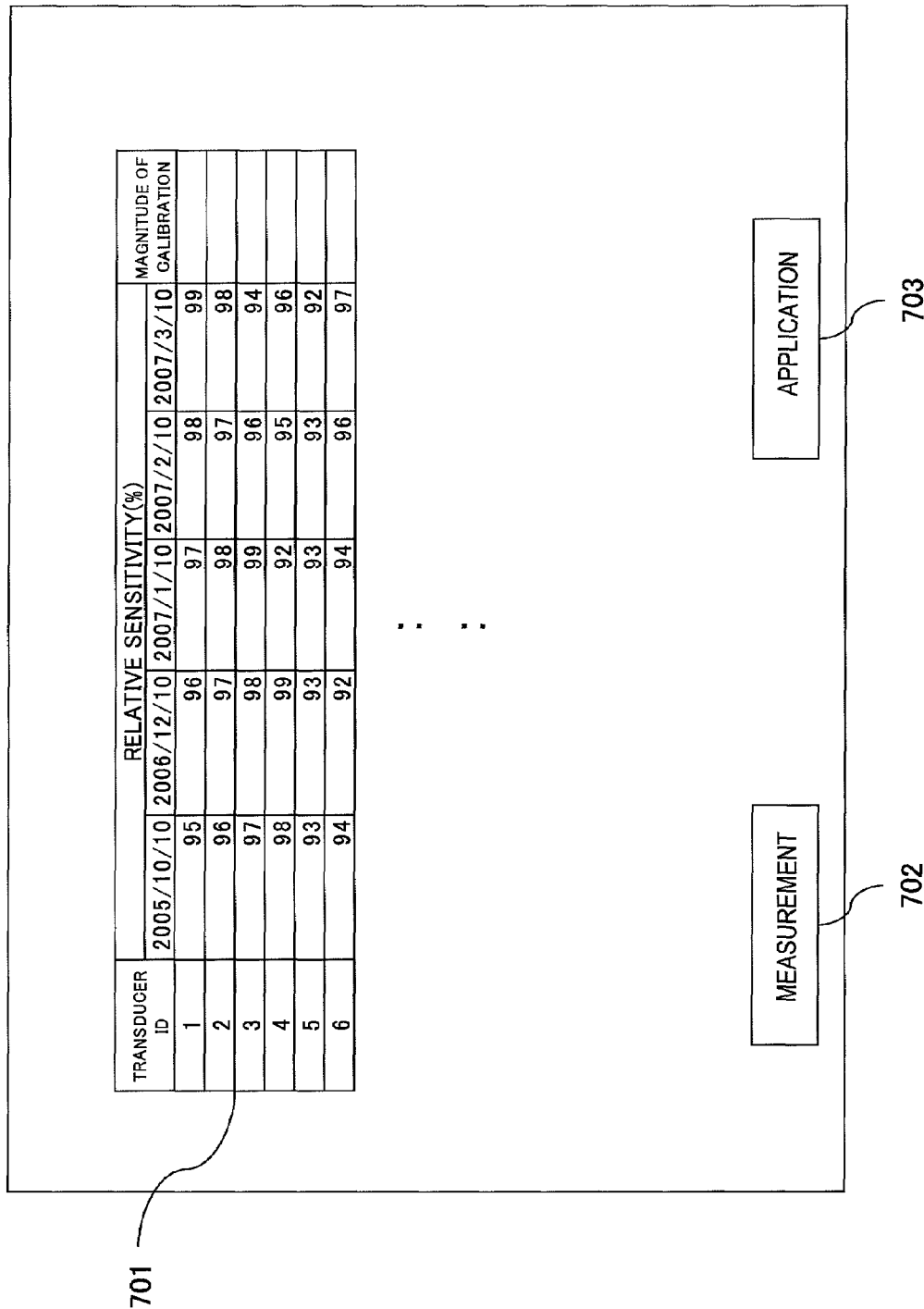
FIG. 17 shows a list of relative values of transmitting/receiving sensitivities of transducers other than a reference transducer with respect to the transmitting/receiving sensitivity of the reference transducer.

1 Vibrational Element
1-a Upper Electrode
1-b Lower Electrode
2 Bias Means
4 Transmission Means
5 Reception Means
6 Transmission/Reception separation Means
7 Transmitting/Receiving Sensitivity Control Circuit

The invention claimed is:
1. An ultrasonic probe having a plurality of transducers, each of which includes a plurality of vibrational elements formed on a substrate that each transmits or receives ultrasonic waves by converting ultrasonic waves and an electric signal into each other with a bias voltage applied thereto, set in array, comprising:
 a transmitting/receiving sensitivity correction means that independently adjusts the bias voltage to be applied to at least two vibrational elements among the plurality of vibrational elements, and corrects a variance in transmitting/receiving sensitivity between the at least two vibrational elements,
 wherein based on the capacitance of a reference vibrational element selected from the at least two vibrational elements, the transmitting/receiving sensitivity correction means corrects the transmitting/receiving sensitivity of the other vibrational elements, and wherein at least a part of the transmitting/receiving sensitivity correction means is disposed outside of the substrate.

2. The ultrasonic probe according to claim 1, wherein according to the transmitting/receiving sensitivities of the at least two vibrational elements, the transmitting/receiving sensitivity correction means converts a DC voltage, which is fed from an externally installed bias means, into a bias voltage of a voltage different from the DC voltage, and applies the converted bias voltage to each of the at least two vibrational elements.

3. The ultrasonic probe according to claim 2, wherein based on the capacitance of the reference vibrational element selected from the at least two vibrational elements and the capacitance of the other vibrational element, the transmitting/receiving sensitivity correction means converts the DC voltage into a bias voltage to be applied to the other vibrational element.

4. The ultrasonic probe according to claim 2, wherein the transmitting/receiving sensitivity correction means includes at least one resistive element, and adjusts the resistance value of at least one resistive element out of the at least one resistive element so as to adjust the voltage of the bias voltage into which the DC voltage is converted.

5. The ultrasonic probe according to claim 4, wherein the transmitting/receiving sensitivity correction means uses the at least one resistive element to be adjusted to perform voltage division on the DC voltage and convert it into the bias voltage.

6. The ultrasonic probe according to claim 4, wherein the transmitting/receiving sensitivity correction means uses an emitter follower circuit, which includes at least one resistive element to be adjusted and a transistor, to convert the DC voltage into the bias voltage.

7. The ultrasonic probe according to claim 4, wherein the transmitting/receiving sensitivity correction means uses a constant voltage circuit, which includes at least one resistive element to be adjusted and an operational amplifier, to convert the DC voltage into the bias voltage.

8. The ultrasonic probe according to claim 4, wherein the transmitting/receiving sensitivity correction means uses a voltage limit circuit, which includes at least one resistive element to be adjusted and a Zener diode, to convert the DC voltage into the bias voltage.

9. The ultrasonic probe according to claim 4, wherein the transmitting/receiving sensitivity correction means uses at least one resistive element to be adjusted and a constant current source to convert the DC voltage into the bias voltage.

10. The ultrasonic probe according to claim 4, wherein:
the at least one resistive element to be adjusted includes a variable resistive element; and
the transmitting/receiving sensitivity correction means includes a resistance value control means that controls the resistance value of the variable resistive element, and controls the resistance value of the variable resistive element so as to adjust the voltage of the bias voltage into which the DC voltage is converted.

11. The ultrasonic probe according to claim 10, wherein:
the variable resistive element includes a thermistor whose resistance value varies depending on temperature; and
the resistance value control means includes a means for controlling the temperature of the thermistor.

12. The ultrasonic probe according to claim 10, wherein the resistive element is formed in the same wafer as the vibrational element is, and exhibits a resistance value adjusted in advance.

13. The ultrasonic probe according to claim 4, wherein:
the resistive element includes a plurality of analog switches; and
the resistance value control means controls the resistance value of the resistive element by switching the switches.

14. The ultrasonic probe according to claim 2, wherein the transmitting/receiving sensitivity correction means includes at least one resistive element, a Zener diode, and a constant current source, and controls the constant current source so as to convert the DC voltage into the bias voltage.

15. The ultrasonic probe according to claim 1, wherein:
the plurality of vibrational elements each includes electrodes;
at least one vibrational element group in which the electrodes of at least one vibrational element among the plurality of vibrational elements are connected in common is formed; and
the transmitting/receiving sensitivity correction means is included in the at least one vibrational element group, and applies the bias voltage to each of the common electrodes of the at least one vibrational element group.

16. The ultrasonic probe according to claim 1, wherein:
the plurality of vibrational elements each includes electrodes;
the electrodes of a plurality of vibrational elements constituting a transducer are connected in common; and
the transmitting/receiving sensitivity correction means is included in at least one transducer among the plurality of transducers, and applies the bias voltage to each of the common electrodes of the at least one transducer.

17. An ultrasonic diagnosis apparatus comprising:
an ultrasonic probe having a plurality of transducers, each of which includes at least one vibrational element that formed on a substrate transmits or receives ultrasonic waves by converting ultrasonic waves and an electric signal into each other with a bias voltage applied thereto, set in array;
a bias means that generates a DC voltage for use in feeding the bias voltage; and
a transmission/reception control means that transmits or receives the electric signal to or from the plurality of vibrational elements,
wherein inside of the probe and between the bias means and the substrate, at least a part of a transmitting/receiving sensitivity correction means that independently adjusts the bias voltage to be applied to the at least two vibrational elements so as to correct a variance in transmitting/receiving sensitivity between the at least two vibrational elements is interposed, and
wherein the transmitting/receiving sensitivity correction means corrects the transmitting/receiving sensitivity of the other vibrational elements based on the capacitance of a reference vibrational element selected from the at least two vibrational elements.

18. The ultrasonic diagnosis apparatus according to claim 17, wherein according to the transmitting/receiving sensitivities of the at least two vibrational elements, the transmitting/receiving sensitivity correction means converts a DC voltage, which is fed from the bias means, into a bias voltage of a voltage different from the DC voltage, and applies the converted bias voltage to each of the at least two vibrational elements.

19. The ultrasonic diagnosis apparatus according to claim 17, wherein the transmitting/receiving sensitivity correction means includes a variation means that adjusts the bias voltage and a memory in which the transmitting/receiving sensitivity characteristics of the vibrational elements are stored, and adjusts the variation means according to information read from the memory so as to correct a variance in transmitting/receiving sensitivity.

20. The ultrasonic diagnosis apparatus according to claim 17, comprising a communication means that communicates with an external control apparatus installed in a place different from a place in which the ultrasonic diagnosis apparatus is installed, wherein:

based on information from the external control apparatus, the transmitting/receiving sensitivity correction means corrects a variance in transmitting/receiving sensitivity between the at least two vibrational elements.

\* \* \* \* \*